United States Patent
Birk

(10) Patent No.: US 8,282,666 B2
(45) Date of Patent: Oct. 9, 2012

(54) PRESSURE SENSING INTRAGASTRIC BALLOON

(75) Inventor: Janel A. Birk, Oxnard, CA (US)

(73) Assignee: Allergan, Inc., Irvine, CA (US)

( * ) Notice: Subject to any disclaimer, the term of this patent is extended or adjusted under 35 U.S.C. 154(b) by 648 days.

(21) Appl. No.: 12/255,209

(22) Filed: Oct. 21, 2008

(65) Prior Publication Data

US 2009/0131968 A1 May 21, 2009

Related U.S. Application Data

(60) Provisional application No. 60/982,005, filed on Oct. 23, 2007.

(51) Int. Cl.
*A61M 29/00* (2006.01)

(52) U.S. Cl. .......................... 606/192; 600/37

(58) Field of Classification Search .................. 606/191, 606/192, 195, 196, 198, 151, 153; 623/23.65, 623/23.66, 23.67; 604/93.01, 96.01, 97.01, 604/99.01; 600/31, 37, 115, 116, 593

See application file for complete search history.

(56) References Cited

U.S. PATENT DOCUMENTS

| | | | |
|---|---|---|---|
| 1,702,974 A | 2/1929 | MacDonald | |
| 3,919,724 A | 11/1975 | Sanders et al. | |
| 4,430,392 A | 2/1984 | Kelley et al. | |
| 4,485,805 A | 12/1984 | Foster, Jr. | |
| 4,607,618 A | 8/1986 | Angelchik | |
| 4,636,213 A | 1/1987 | Pakiam | |
| 4,694,827 A * | 9/1987 | Weiner et al. ................. | 606/192 |
| 4,930,535 A | 6/1990 | Rinehold | |
| 4,969,899 A | 11/1990 | Cox, Jr. | |
| 5,084,061 A | 1/1992 | Gau et al. | |
| 5,211,371 A | 5/1993 | Coffee | |
| 5,725,507 A | 3/1998 | Petrick | |
| 5,819,749 A | 10/1998 | Lee et al. | |
| 6,102,897 A | 8/2000 | Lang | |
| 6,454,785 B2 | 9/2002 | DeHoyos Garza | |
| 6,579,301 B1 * | 6/2003 | Bales et al. .................... | 606/191 |
| 6,629,776 B2 | 10/2003 | Bell et al. | |
| 6,733,512 B2 * | 5/2004 | McGhan ....................... | 606/192 |

(Continued)

FOREIGN PATENT DOCUMENTS

DE 88 04 765 U1 5/1989

(Continued)

OTHER PUBLICATIONS

Patient Information Brochure, "Living With the Bib/BioEnterics Intragastric Balloon Program," Inamed Health, May 1, 2005, 1-10 pp.

(Continued)

*Primary Examiner* — Gary Jackson
*Assistant Examiner* — Katrina Stransky
(74) *Attorney, Agent, or Firm* — Stephen Donovan; Debra Condino

(57) ABSTRACT

An intragastric balloon having a built-in sensor. The sensor may be used to monitor pressure within the balloon shell, or outside of the shell in the stomach. The sensor may be used after deflation of the intragastric balloon to monitor the pressure through the intestinal tract as the balloon migrates therethrough. An apparatus for remote deflation of the balloon may be utilized to allow a physician to deflate the intragastric balloon without surgery. The pressure sensor may be provided in a valve of the intragastric balloon which separates from the balloon and migrates as a capsule through the intestinal tract to monitor conditions therein.

5 Claims, 13 Drawing Sheets

U.S. PATENT DOCUMENTS

| | | | |
|---|---|---|---|
| 6,733,513 B2 | 5/2004 | McGhan | |
| 6,746,460 B2 | 6/2004 | Gannoe et al. | |
| 6,840,257 B2 | 1/2005 | Dario et al. | |
| 6,994,095 B2* | 2/2006 | Burnett | 128/898 |
| 7,020,531 B1 | 3/2006 | Colliou et al. | |
| 7,037,344 B2 | 5/2006 | Kagan et al. | |
| 7,056,305 B2 | 6/2006 | Garza Alvarez | |
| 7,214,233 B2 | 5/2007 | Gannoe et al. | |
| 7,854,745 B2* | 12/2010 | Brister et al. | 606/196 |
| 2002/0198470 A1* | 12/2002 | Imran et al. | 600/587 |
| 2003/0106761 A1 | 6/2003 | Taylor | |
| 2004/0102677 A1* | 5/2004 | Frering | 600/31 |
| 2004/0162469 A1* | 8/2004 | Imran | 600/310 |
| 2005/0055039 A1 | 3/2005 | Burnett et al. | |
| 2005/0190070 A1 | 9/2005 | Rudduck et al. | |
| 2005/0192615 A1 | 9/2005 | Torre et al. | |
| 2005/0240279 A1 | 10/2005 | Kagan et al. | |
| 2005/0250979 A1 | 11/2005 | Coe | |
| 2005/0267595 A1 | 12/2005 | Chen et al. | |
| 2005/0267596 A1 | 12/2005 | Chen et al. | |
| 2006/0069403 A1* | 3/2006 | Shalon et al. | 606/192 |
| 2006/0142700 A1 | 6/2006 | Sobelman et al. | |
| 2007/0016262 A1 | 1/2007 | Gross et al. | |
| 2007/0083224 A1 | 4/2007 | Hively | |
| 2007/0100369 A1 | 5/2007 | Cragg et al. | |
| 2007/0147170 A1 | 6/2007 | Hood et al. | |
| 2007/0156248 A1 | 7/2007 | Marco et al. | |
| 2008/0306506 A1* | 12/2008 | Leatherman | 606/192 |

FOREIGN PATENT DOCUMENTS

| | | |
|---|---|---|
| WO | WO2005/007231 | 1/2005 |
| WO | WO2006/063593 | 6/2006 |

OTHER PUBLICATIONS

Bib Data Sheet Directions for Use, "BioEnterics Intragastric Balloon System," Inamed Health, 1-12 pp., Feb. 1, 2005.

Bib Bioenterics Intragastric Balloon Program, "Taking the Next Step/Take Control of Your Weight and Your Life," Inamed Health, Apr. 29, 2004, 1-9 pp.

Bib Bioenterics Intragastric Balloon Program, "Take Control of Your Weight and Your Life/The Solution for You," Inamed Health, Jan. 19, 2004, 1-2 pp.

* cited by examiner

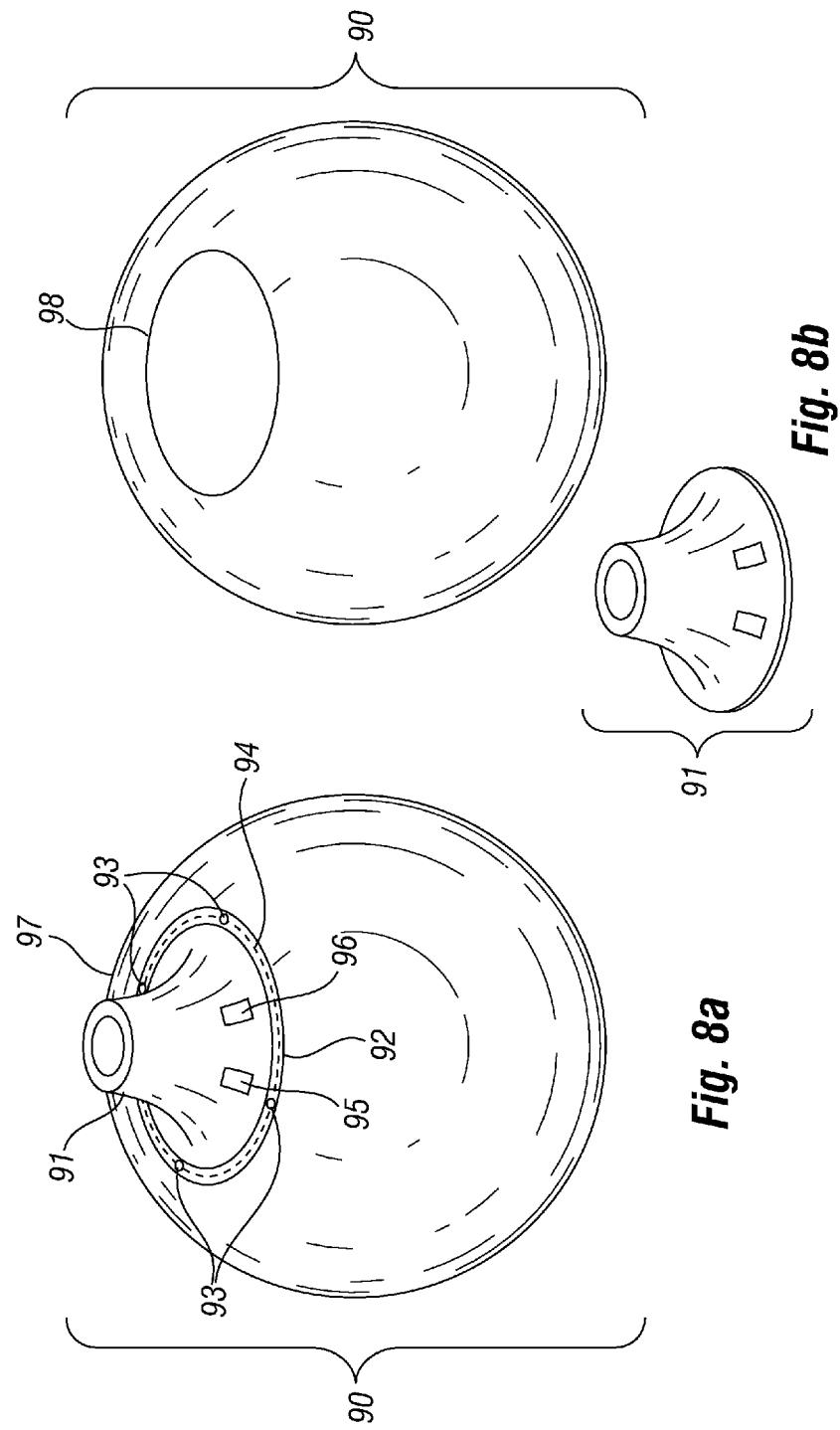

PRESSURE SENSING INTRAGASTRIC BALLOON

RELATED APPLICATION

This application claims priority to U.S. Provisional Application Ser. No. 60/982,005 filed on Oct. 23, 2007 and which is incorporated herein by reference.

FIELD OF THE INVENTION

The present invention is directed to intragastric balloons used for the treatment of obesity, and in particular to devices and methods for monitoring internal pressures using an implanted intragastric balloon.

BACKGROUND OF THE INVENTION

Intragastric balloons are well known in the art as a means for treating obesity. One such inflatable intragastric balloon is described in U.S. Pat. No. 5,084,061 and is commercially available as the BioEnterics Intragastric Balloon System (sold under the trademark BIB® System). These devices are designed to provide therapy for moderately obese individuals who need to shed pounds in preparation for surgery, or as part of a dietary or behavioral modification program.

The BIB System, for example, comprises a silicone elastomer intragastric balloon that is inserted into the stomach and filled with fluid. Conventionally, the balloons are placed in the stomach in an empty or deflated state and thereafter filled (fully or partially) with a suitable fluid. The balloon occupies space in the stomach, thereby leaving less room available for food and creating a feeling of satiety for the patient. Clinical results with these devices show that for many obese patients, the intragastric balloons significantly help to control appetite and accomplish weight loss.

Placement of such balloons is temporary, and such balloons are typically removed after about six months. One means of removing the balloon is to deflate it by puncturing the balloon, and either aspirating the contents of the balloon or allowing the fluid to pass into the patient's stomach. This means of removing fluid from the balloon requires surgical intervention, through the use of a gastroscopic instrument. Alternatively, if the balloon is left in place beyond its designed lifetime, the acids present in a patient's stomach may erode the balloon to the point where it self deflates. When this occurs, the deflated balloon may pass naturally through the patient's digestive system and be expelled through the bowel. For instance, McGhan, U.S. Pat. No. 6,733,512, describes a self-deflating intragastric balloon that includes a biodegradable inflation valve. After a certain residence time in the stomach, the valve starts to leak and eventually the balloon deflates and passes though the patient's digestive tract.

Despite the advances in the design of intragastric balloons, there remains a need for improved intragastric balloon systems and methods.

SUMMARY OF THE INVENTION

The present invention addresses the above-described problems by providing apparatuses and methods for the remote deflation of an intragastric balloon. The present invention allows a physician to remotely deflate an intragastric balloon from outside the body, utilizing a remote control that triggers the deflation with an activation signal.

In accordance with one aspect of the invention, a sensor attached to the balloon monitors conditions within or external to the balloon shell. For instance, a pressure sensor may monitor pressure within the balloon and provide valuable information regarding potential leaking from the balloon. The sensor may be incorporated in a detachable deflation valve and used to monitor conditions through the gastrointestinal (GI) tract as the valve passes.

One aspect of the invention comprises an inflatable intragastric balloon useful for facilitating weight loss in a patient in need thereof. The intragastric balloon has a shell for containing a volume of fluid introduced therein, a valve for adjusting the volume of fluid in the shell, and a sensor for measuring a condition of fluid in the shell. In one embodiment, a remote control outside the patient's body communicates with a deflation mechanism to empty the volume of fluid in the shell through the valve. The remote control may also communicate with the sensor, and the sensor may be coupled to a microchip capable of writing data, wherein the remote control can read from the microchip.

In one embodiment, the sensor is located on the valve. There may be more than one sensor, one of which measures a condition of fluid in the shell and one of which measures a condition of an environment external to the shell. In one embodiment, the valve is in a self-contained capsule that may be separated from the shell by a remotely-activated mechanism, thereby deflating the shell.

A second aspect of the invention is an inflatable intragastric balloon comprising a shell for containing a volume of fluid introduced therein, a self-contained capsule attached to the shell that may be separated from the shell, thereby deflating the shell, and a pressure sensor in the capsule. The intragastric balloon may also have a valve attached to the shell and a remote control outside the patient's body communicates with a deflation mechanism to empty the volume of fluid in the shell through the valve. The remote control may also communicate with the sensor. Also, the valve may be provided in the capsule. There may be more than one pressure sensor, one of which measures pressure in the shell and one of which measures pressure external to the shell, when the capsule is attached to the shell. The capsule may be separated from the shell by a remotely-activated mechanism.

A method of the invention for the monitoring an intragastric balloon containing a volume of fluid therein comprises inserting an intragastric balloon into a patient's stomach. The intragastric balloon has a shell for containing a volume of fluid introduced therein, a valve on the shell for adjusting the volume of fluid in the shell, and a sensor on the shell for measuring the pressure of fluid in the shell. The method includes measuring the pressure of fluid in the shell, and may further include adjusting the volume of fluid within the shell based on the pressure measured. The method of adjusting the volume of fluid within the shell may alternatively include manually adjusting the pressure using an instrument to access the balloon, remotely controlling the valve to adjust the volume of fluid, or providing an internal power source and microchip for collecting data on the measured pressures and controlling the valve autonomously. The intragastric balloon may include a mechanism that permits remote adjustment of the volume of fluid in the shell through the valve, the method further including remotely activating the mechanism to adjust the volume of fluid in the shell.

The method may also include creating an opening in the shell, allowing normal intragastric movements to drain fluid from the balloon through the opening, allowing the deflated balloon to pass through the gastrointestinal tract, and measuring pressures in the gastrointestinal tract as the sensor passes therethrough. A self-contained capsule may be on the shell that may be separated from the shell, thereby creating the opening in the shell. In one embodiment, the sensor is located on the capsule and the step of measuring pressures in the gastrointestinal tract is done as the capsule passes therethrough. The intragastric balloon may have a remotely-activated mechanism for separating the capsule from the shell, and the method further includes remotely separating the capsule from the shell.

Another method of the invention comprises inserting an intragastric balloon into a patient's stomach, the intragastric balloon having a shell for containing a volume of fluid introduced therein, a self-contained capsule attached to the shell that may be separated from the shell, and a sensor located on the capsule. The method comprises measuring a condition of fluid in the shell with the sensor, separating the capsule from the shell to create an opening in the shell and permit deflation of the shell, allowing the capsule to pass through the gastrointestinal tract, and measuring conditions in the gastrointestinal tract with the sensor as the capsule passes therethrough. The intragastric balloon also may have a valve on the shell for adjusting the volume of fluid in the shell, and the method includes adjusting the volume of fluid within the shell based on the measured condition of fluid in the shell. The intragastric balloon may include a mechanism that permits remote adjustment of the volume of fluid in the shell through the valve, and the method involves remotely activating the mechanism to adjust the volume of fluid in the shell. In one embodiment, the sensor is coupled to a microchip capable of writing data, and the method includes remotely reading from the microchip.

In a still further embodiment, the apparatus of the present invention includes a meltable wax plug that melts to cause the opening of a valve. Upon receipt of an activation signal sent by the physician from a remote control outside the body, the microelectronics contained in the valve assembly cause the temperature of heating element(s) contained within the valve to melt the wax plug. Once the wax plug has melted, thus causing the balloon valve to open, the normal movements of the stomach cause the fluid contained within the balloon to empty from the balloon, causing deflation. The patient is able to then pass the balloon.

In another embodiment, the apparatus of the present invention includes a remote deflation valve having a shape memory element spring that holds a plug in place, thus sealing the valve of the intragastric balloon. The shape memory element spring may be heated remotely by induction, or the deflation mechanism may include microelectronics to cause heating of the spring. As the spring changes shape as a result of the application of heat, it removes the plug, thus causing the balloon to unseal. The fluid contained in the balloon may then flow freely out of the balloon, thus causing the balloon to deflate. The patient is then able to safely pass the deflated balloon.

According to yet another embodiment of the present invention, the intragastric balloon includes a remote deflation mechanism with a shape memory element actuator, a spring collar, an obstruction that holds the spring collar in place and a slit valve. As with the other embodiments disclosed, the shape memory element actuator may be heated remotely by induction or may alternatively include microelectronics and heating elements contained within the deflation mechanism. When the deflation mechanism is activated, the actuator pushes the obstruction out of the valve, thus allowing the spring collar to contract. The contraction of the spring collar causes the slit valve to open, which allows fluid contained in the balloon to flow out of the balloon and drain accordingly. The patient is then able to pass the deflated balloon.

In another embodiment of the present invention, a shape memory element "cutting wire" is employed in the remote deflation mechanism. In this embodiment, when heat is applied to the shape memory alloy wire contained within a remote deflation valve, the wire changes shape, causing the wire to cut through a wax (or other suitable material, e.g. plastic or polymer) plug that seals the valve. Once the wax plug has been cut from the valve, fluid is able to freely flow through the valve, thus allowing the balloon to drain and pass from the body.

In still yet another embodiment of the present invention, the remote deflation mechanism of the intragastric balloon includes a wire that surrounds the valve. The wire is used to break the bond between the valve and the balloon. When the bond between balloon and the valve is broken, the valve separates from the balloon, and fluid flows freely from the balloon. This embodiment has the added benefit that the balloon and valve assembly may pass through the body separately, thus allowing passage to occur more easily, as the device is in two separate pieces. These and various other aspects of the invention, and its advantages, will be discussed in more detail below.

In another embodiment, the valve could be contained in a cylindrical capsule (taking the shape of a large pill, for example) that fits within a collared opening of the balloon shell to create a seal. The collared opening could include a spring or other such mechanism that would retain the size and shape of the collar. When the remote deflation mechanism is activated, the spring is released, thereby opening the collar and ejecting the cylindrical capsule from the balloon, rendering two separate components that could then easily pass through the gastrointestinal track. Alternatively, the collared opening could include a heating element, which when the remote deflation mechanism is activated, would cause the seal between the capsule and the collar to break, thereby ejecting the cylindrical capsule from the balloon. As yet a further alternative, the cylindrical capsule could contain a mechanism such as a spring (a torsional spring, for example), that retains the shape and size of the capsule, holding the capsule in place within the collared opening of the balloon shell. When the remote deflation mechanism is activated, the torsional spring collapses, causing the capsule to be ejected from the balloon.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

FIG. 8a shows an elevated side view of an intragastric balloon of the present invention with a deflation mechanism surrounding the valve prior to the deflation mechanism being activated.

FIG. 8b shows an elevated side view of FIG. 8a after the deflation mechanism has been activated.

DETAILED DESCRIPTION

The present invention is directed to a method and device for sensing conditions such as pressure in and around an intragastric balloon, potentially in conjunction with remotely deflating the intragastric balloon without surgical intervention, as disclosed in U.S. application Ser. No. 11/735,194, filed Apr. 13, 2007, the disclosure of which is expressly incorporated by reference herein.

Figure 1:
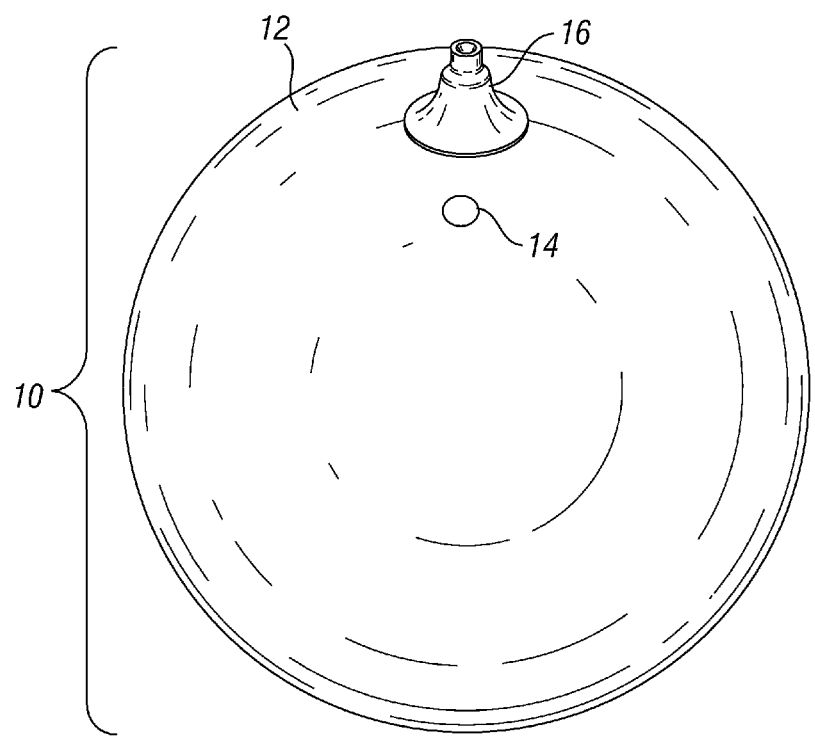
FIG. 1 is an elevated side view of an intragastric balloon of the present invention.
Figure 2A:
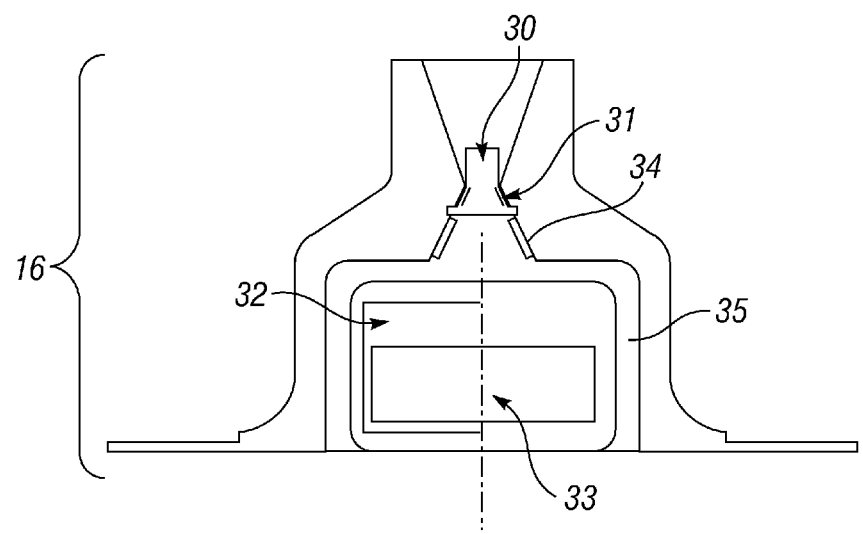
FIG. 2a is a side cut-away view of a remote deflation valve according to one embodiment of the present invention, which shows the valve in the "closed" position.
Figure 2B:
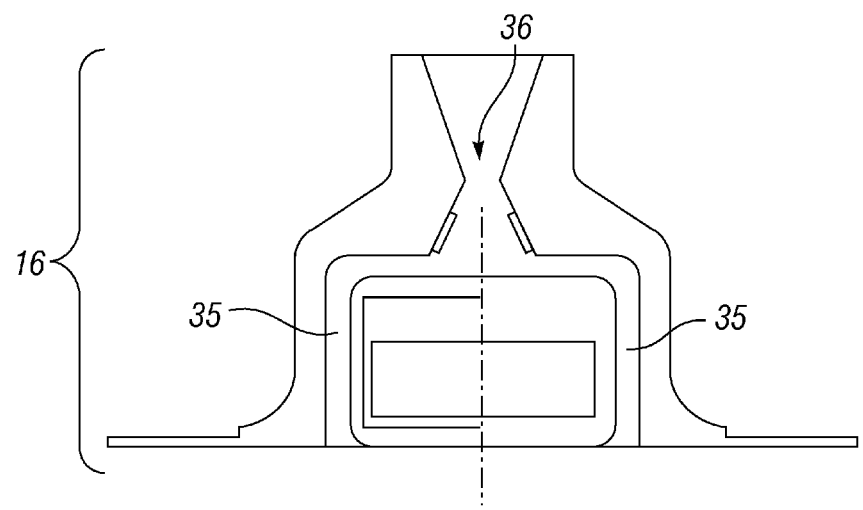
FIG. 2b is a side cut-away view of the remote deflation valve of FIG. 2a shown in the "open" position.

Referring to FIGS. 1-2b, the intragastric balloon according to one embodiment of the present invention is shown. The intragastric balloon 10 includes a shell 12, fill valve 14, and remote deflation valve 16.

During implantation, an un-inflated balloon 10 may be positioned in the stomach in a desired location. Once the balloon is positioned, it may be inflated using fill valve 14, and those experienced in the art will appreciate that there are several different methods for inflating the balloon, such as disclosed in commonly assigned U.S. Patent Publication 2006-0142700, entitled "Two Way Slit Valve", the disclosure of which is incorporated in its entirety herein by reference.

After implantation, it may become desirable to remove the balloon. In order to remove the balloon it must first be deflated. Once deflated, the balloon may be allowed to naturally pass through the body upon deflation, or alternatively the balloon may be surgically removed using a minimally invasive gastroscopic procedure. The present invention is designed such that the deflated intragastric balloon and integrated remote deflation valve, either together or separately, may naturally pass through the human body.

Referring to FIGS. 2a and 2b, one embodiment of the remote deflation valve of the present invention is shown. Remote deflation valve 16 is comprised of sealing plug 30, heating element(s) 31, microelectronic control 32 and power source 33. The power source 33 may be a battery, capacitor, induction coil, kinetic energy creation by body motion stored onto a capacitor, fuel cell, power source powered by chemistry of the body, or a power source powered by temperature change. The sealing plug 30 may be formed of suitable medical-grade wax, such as paraffin, or may also be a lower temperature melt polymer. Any type of suitable medical-grade wax, such as paraffin, may be used for sealing plug 30.

At the time the physician desires to deflate the balloon, the patient may be brought into the physician's office in an outpatient setting. In order to open deflation valve 16, the physician activates the valve opening mechanism remotely and from outside the body, using a remote control 100 such as that depicted in FIG. 9. The physician holds remote control 100 near the stomach of the patient, and upon depression of button 101, remote control 100 sends an activation signal, which my be comprised of radio waves, sonic waves, or any other waves suitable for transmitting a small activation signal through the tissue of the abdominal cavity to the implanted balloon.

Microelectronic control 32 has an antenna (not shown) for receiving the activation signal from remote control 100. Upon receiving the activation signal, microelectronic control uses power from power source 33 to begin increasing the temperature of the heating element(s) 31. A metal film heating element utilizing metals (such as nichrome, stainless steel, copper, gold, etc.) can be used for heating element(s) 31. As the temperature of the heating element(s) 31 begins to increase, the sealing plug 30 begins to melt. Ideally, the melting point of the sealing plug will be slightly above the temperatures in the stomach to ensure that the valve stays closed in its normal operating environment.

As the sealing plug begins to melt, it is expelled into the stomach and/or collects on wicking surfaces 34, which may be composed of a contoured reservoir. Ideally the wax will melt and be expelled into the stomach for rapid quench cooling and passage through the intestines. The collection of the wax or other sealing material on wicking surfaces 34 prevents it from clogging capillaries 35 and allows the fluid contained within intragastric balloon 10 to flow out of the balloon. Once the sealing plug is completely melted and been expelled into the stomach and/or collected on wicking surfaces 34, capillaries 35 allow the free flow of the fluid contained inside the balloon through valve opening 36 (FIG. 2*b*). Through the normal movements and contraction of the stomach walls, the balloon will drain of the fluid contained inside and shrink down to a size that is passable through the body. The microelectronics, heating element, and power source are safely contained within the valve structure such that they do not present any danger to the patient.

In addition to performing the function of controlling the heating element for the melting of the sealing plug, the microelectronic control 32 may communicate with the remote control 100 to confirm that the deflation mechanism has been activated. Following receipt of a confirmation signal, the physician and patient may then track the progress of the passing of the device.

Figure 3A:
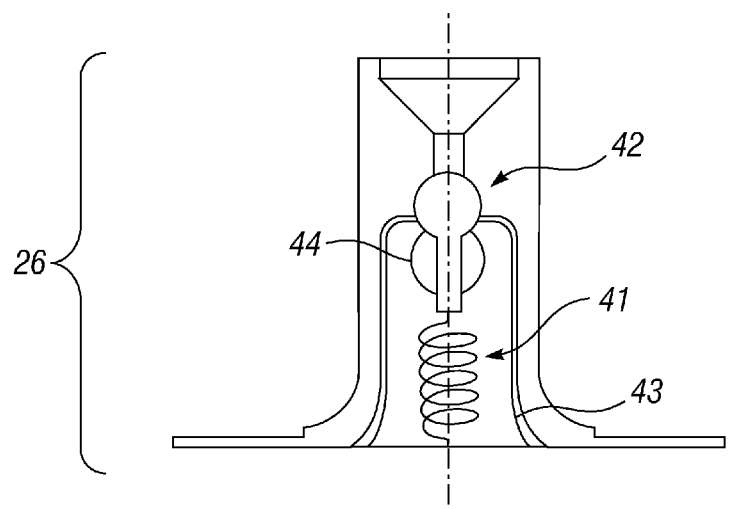
FIG. 3a is a side cut-away view of a remote deflation valve according to a further embodiment of the present invention, which shows the valve in the "closed" position.
Figure 3B:
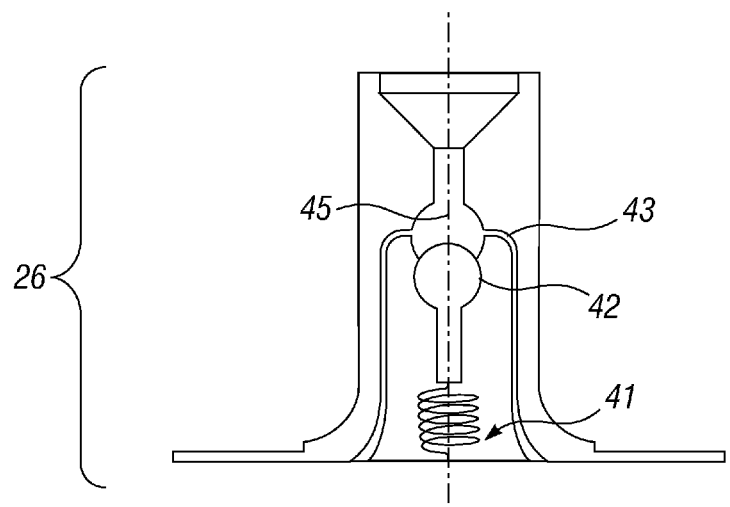
FIG. 3b is a side cut-away view of the remote deflation valve of FIG. 3a shown in the "open" position.

Referring to FIGS. 3*a* and 3*b*, another embodiment of the remote deflation valve of the present invention is shown. Remote deflation valve 26 is comprised of a shape memory spring 41, plug 42, and capillaries 43. While NITINOL is one suitable material for the spring utilized in the present invention, any number of shape memory alloys or polymers, or spring materials, including steels (such as stainless steel, chromium, titanium, etc.), may be used.

As with the valve mechanism discussed in the previous embodiment, at the time the physician desires to deflate the balloon, the patient may be brought into the physician's office in an outpatient setting.

In order to open deflation valve 26, the physician activates the deflation mechanism from outside the body, using a remote control (not shown). The spring may be heated remotely by induction from the remote control, or may alternatively include microelectronics for receiving an activation signal and controlling heating elements similar to those described in the previous embodiment.

Irrespective of the method of activation, when the spring 41 is heated, it contracts, pulling the plug 42 out of its resting place and into reservoir 44. This causes channel 45 to open, thus allowing the fluid contained in the balloon to flow through the capillaries 43 and open channel 45, out of the balloon. FIG. 3*b* shows the valve mechanism in its open position. Because of pressure normally exerted on the balloon by the stomach, the fluid contained therein will flow freely through the capillaries and open channel and into the stomach, thus causing the balloon to deflate. The deflated intragastric balloon is then allowed to pass out of the body.

As an alternative to having a shape memory spring permanently fixed to a plug, the spring may be detachably fixed to a plug comprised of wax or some other similar biodegradable material. In this way, when the spring is heated and changes shape, it may be used to eject the biodegradable plug into the stomach, thus allowing the balloon to drain. The deflated intragastric balloon would then be allowed to pass out of the body.

Figure 4A:
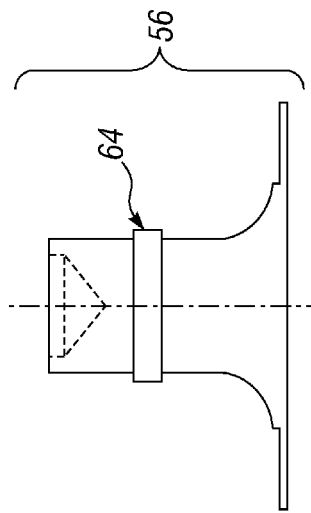
FIG. 4a is a side view of a remote deflation valve according to yet a further embodiment of the present invention, which shows the valve in the "closed" position.
Figure 5A:
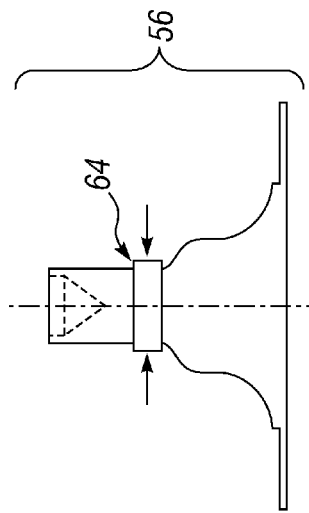
FIG. 5a is a side view of the remote deflation valve of FIG. 4a which shows the valve in the "closed" position.
Figure 4B:
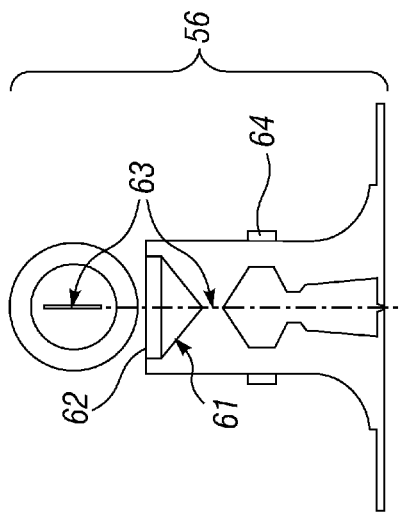
FIG. 4b is a side cut-away view of the remote deflation valve of FIG. 4a shown in the "open" position.
Figure 5B:
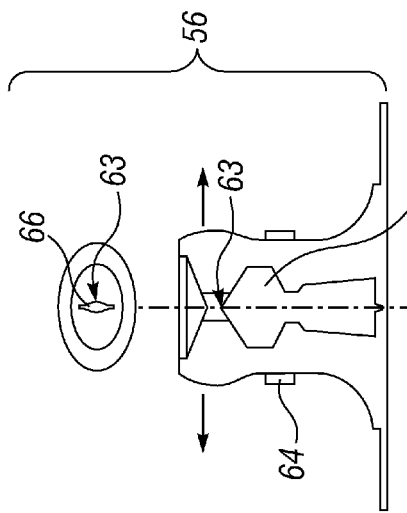
FIG. 5b is a side view of the remote deflation valve of FIG. 4b shown in the "open" position.

Referring to FIGS. 4*a*, 4*b*, 5*a*, and 5*b*, another embodiment of a remote deflation valve of the present invention is shown. FIGS. 4*a* and 4*b* show a cutaway side view of remote deflation valve 56, while FIGS. 5*a* and 5*b* show the same valve in a side view. Remote deflation valve 56 is comprised of a shape memory actuator 61, obstruction 62, slit valve 63 and spring collar 64. As previously discussed, while NITINOL is one suitable material for the actuator of the present invention, any number of shape memory alloys or polymers may be used.

In order to open deflation valve 56, the physician activates the valve opening mechanism remotely and from outside the body, using remote control 100. The actuator 61 may be heated remotely by induction or alternatively the remote deflation valve may include microelectronics and heating elements.

Irrespective of the method of activation, the actuator 61, when activated, pushes obstruction 62 out of the valve opening. When in place, obstruction 62 serves to prevent the slit valve 63 from opening by causing spring collar 64 to be held in its open position, as shown in FIGS. 4*a* and 5*a*. Once the obstruction 62 is removed from the valve opening, spring collar 64, which is located below the slit valve 63, contracts. The contraction of spring collar 64 causes the slit valve 63 to be opened, as shown in FIGS. 4*b* and 5*b*. With the slit valve 63 now open, the fluid contained in the balloon may flow through channel 65 and out through the slit valve opening 66. Again, because the intragastric balloon is under pressure, and due to the normal movements of the stomach, the fluid contained therein will flow freely through open slit valve 63 and into the stomach, thus causing the balloon to deflate. The deflated intragastric balloon is then allowed to pass out of the body.

Figure 6A:
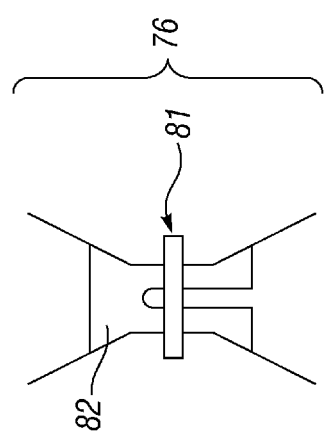
FIG. 6a is a side cut-away view of a remote deflation valve according to still a further embodiment of the present invention, which shows the valve in the "closed" position.
Figure 6B:
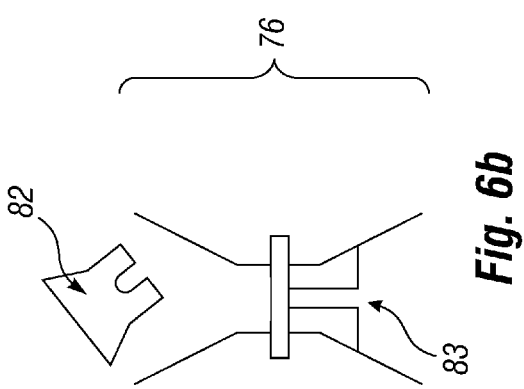
FIG. 6b is a side cut-away view of the remote deflation valve of FIG. 6a shown in the "open" position.

Referring to FIGS. 6*a* and 6*b*, an interior cutaway view of another embodiment of the remote deflation valve of the present invention is shown. Remote deflation valve 76 is comprised of a shape memory alloy cutting wire mechanism 81, sealing plug 82, and capillary 83. NITINOL is used in this embodiment, however, any number of suitable shape memory alloys may be used.

Figure 9:
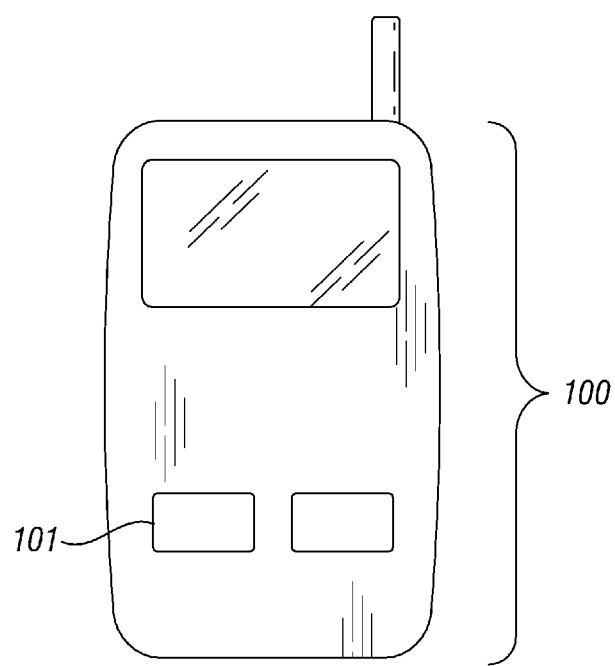
FIG. 9 is a front view of a remote control for activating a remote deflation valve according to the present invention.

As with the previous embodiments discussed, in order to open valve 76, the physician activates the valve opening mechanism remotely and from outside the body, using remote control 100 (FIG. 9). In this embodiment, the remote deflation valve 76 includes microelectronics (not shown), a battery or other power source (not shown) and heating element(s) 85 (FIGS. 7*a*-7*d*) for heating the shape memory alloy cutting wire 84 (FIGS. 7*a*-7*d*). As with the previous embodiments discussed, however, the shape memory alloy cutting wire may be heated by induction.

Figure 7A:
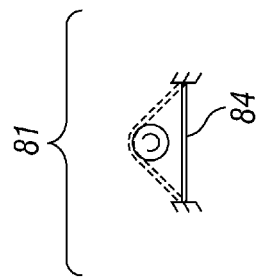
FIGS. 7a and 7b show a top view of an embodiment of the wire cutting mechanism of the remote deflation valve of FIGS. 6a and 6b.
Figure 7B:
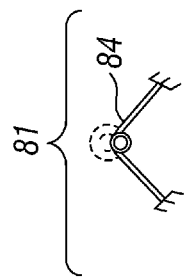
Figure 7C:
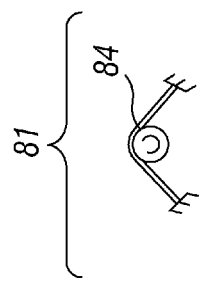
FIGS. 7c and 7d show a further embodiment of the wire cutting mechanism of the remote deflation valve of FIGS. 6a and 6b.

FIGS. 7*a*, 7*b*, 7*c*, and 7*d* show top views of the cutting wire mechanism 84. As heat is applied by the heating elements, the shape memory element begins to change shape. FIG. 7*a* shows the shape memory element cutting wire 84 prior to the application of heat. Prior to the application of heat, the shape memory element cutting wire 84 is in a curved L-shape, with the curved portion resting around the outside of wax plug 82. As an alternative to the L-shaped shape memory element cutting wire 84 of FIG. 7*a*, the cutting wire may also be in a loop shape that completely encircles the wax plug, as is shown in FIG. 7*c*.

Figure 7D:
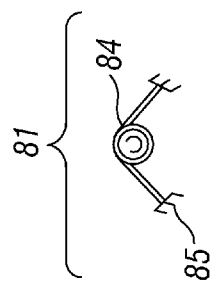

In this embodiment, the shape memory element cutting wire mechanism 81 is activated by a signal received from remote control 100 (FIG. 9). Upon receiving the activation signal, the microelectronic control (not shown) uses power from the power source (not shown) to begin increasing the temperature of heating element(s) 85. As the shape memory element cutting wire 84 begins to change shape as a result of the application of heat, it slices through the sealing plug 82. FIGS. 7*b* and 7*d* show the shape memory alloy cutting wire 84 in its post-heat application deformed shape, having cut through the sealing plug 82. FIG. 7*a* shows a shape memory alloy cutting wire in an L-shaped configuration, while FIG. 7*c* shows a shape memory alloy cutting wire in a loop shaped configuration.

With the sealing plug 82 having been severed from the valve, the capillary 83 (FIG. 6*b*) is now open to allow fluid contained within the intragastric balloon to escape the balloon. Again, because the intragastric balloon is under pressure and due to the normal movements of the stomach, the fluid contained in the balloon will flow freely through the capillary and into the stomach, thus causing the balloon to deflate. The deflated intragastric balloon is then allowed to pass out of the body.

Referring to FIGS. 8*a* and 8*b*, another embodiment of an intragastric balloon of the present invention incorporating a remote deflation mechanism is shown. Intragastric balloon 90 is comprised of shell 97, valve 91, valve/balloon bond 92, heating elements 93, cutting wire 94, microelectronic control 95, and power source 96.

Rather than using a remote deflation mechanism to open the valve of the intragastric balloon, the embodiment of the present invention shown in FIGS. 8*a* and 8*b* utilizes a deflation mechanism for separating the entire valve from the remaining portion of the balloon.

Similar to the procedures described above, at the time the physician desires to deflate the balloon, the patient may be brought into the physician's office in an outpatient setting. In order to cause the intragastric balloon 90 to deflate, the physician activates the valve opening mechanism remotely and from outside the body, using a remote control 100 (FIG. 9). The physician holds remote control 100 near the stomach of the patient, and upon depression of a button, remote control 100 sends an activation signal to the microelectronic control 95.

Microelectronic control 95 has an antenna (not shown) for receiving the activation signal from remote control 100. Upon receiving the activation signal, microelectronic control uses power from power source 96 to begin increasing the temperature of heating element(s) 93. Similar to the embodiments discussed above that incorporate heating elements, metal film heating elements utilizing materials such as nichrome, stainless steel, copper, gold, or other such materials, can be used for heating element(s) 93. As the temperature of heating element(s) 93 begins to increase, the temperature of cutting wire 94 also begins to increase. The increased temperature of the cutting wire causes the valve/balloon bond 92 to deteriorate, resulting in separation of the valve 91 from shell 97.

Once the valve/balloon bond 92 is broken and the valve is separated from the shell, fluid contained inside the balloon freely flows through the opening 98 that is created by the separation of the two portions. Through the normal movements and contraction of the stomach walls, the balloon will drain of the fluid contained inside and shrink down to a size that is passable through the human body. The microelectronics, heating element(s) and power source are safely contained within the valve structure such that they do not present any danger to the patient. Because the entire intragastric balloon may now be in two separate pieces—an empty shell and a self-contained valve assembly—the passing of the balloon and valve is facilitated.

As with the previous embodiments described, in addition to performing the function of controlling the heating elements, the microelectronic control 95 may communicate with the remote control 100 to confirm that the deflation mechanism has been activated. Following receipt of a confirmation signal, the physician and patient may then track the progress of the passing of the device.

Figure 10A:
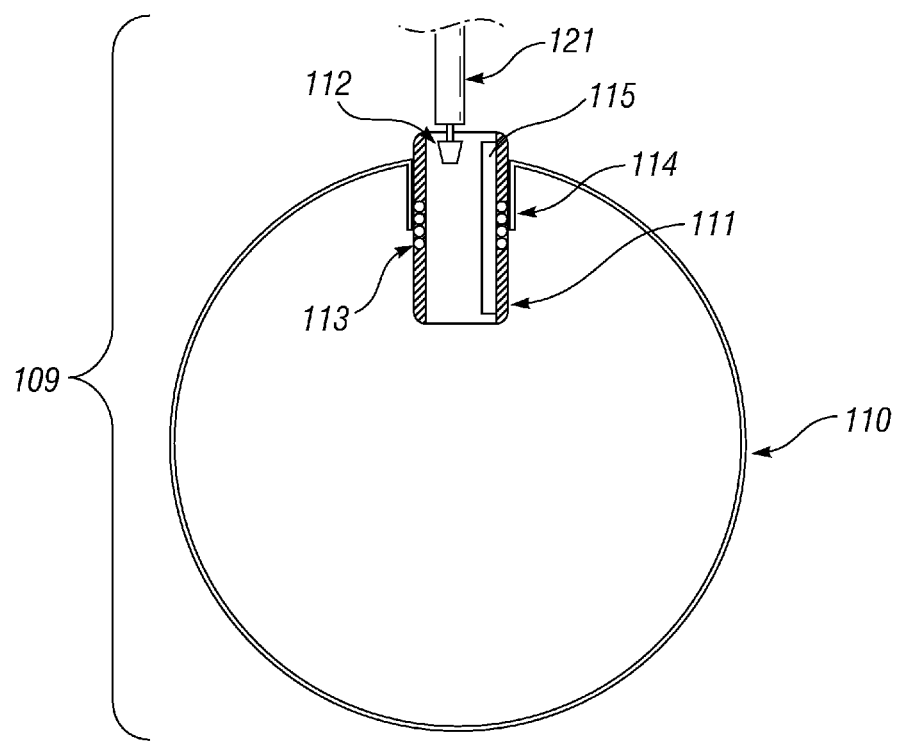
FIG. 10a is a side cut-away view of a remote-deflating intragastric balloon according to still a further embodiment of the present invention, which shows the balloon in the "closed" position.
Figure 10B:
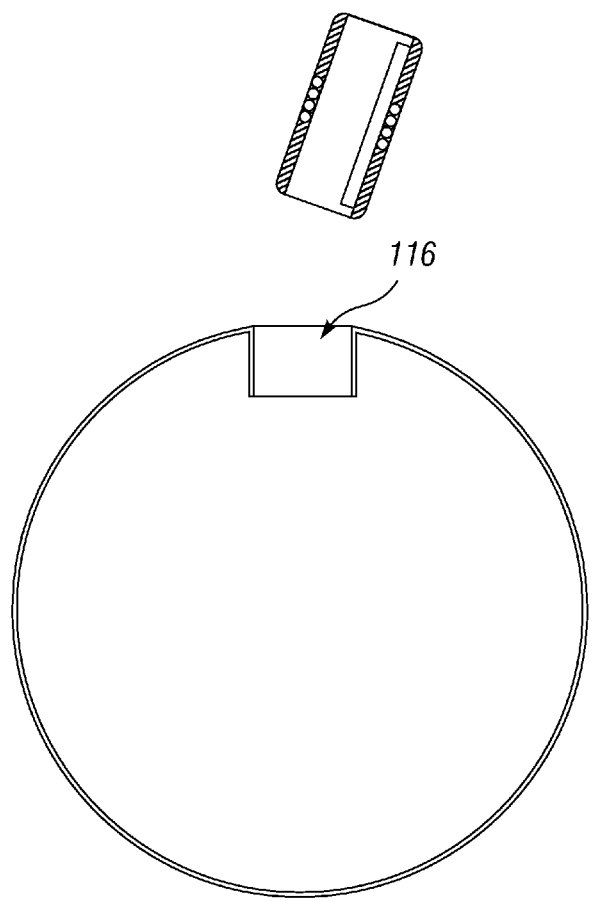
FIG. 10b is a side cut-away view of the remote-deflating intragastric balloon of FIG. 10a shown in the "open" position.

Referring to FIGS. 10*a* and 10*b*, another embodiment of an intragastric balloon of the present invention incorporating a remote deflation mechanism is shown. Intragastric balloon 109 is comprised of shell 110 and valve capsule 111. Valve capsule 111 is comprised of valve 112, shape memory torsional spring 113, and combined microelectronic control and power source 115. FIG. 10*a* also shows adjustment tool 121 for adjusting the volume of the intragastric balloon 109.

Rather than using a remote deflation mechanism to open the valve of the intragastric balloon, the embodiment of the present invention shown in FIGS. 10*a* and 10*b* utilizes a deflation mechanism for separating the entire valve capsule from the remaining portion of the balloon. When inflated, the valve capsule 111 is held tightly in the balloon collar 114 by pressure exerted by shape memory torsional spring 113, creating a seal between the valve capsule and the balloon collar.

Similar to the various procedures described above, at the time the physician desires to deflate the balloon, the patient may be brought into the physician's office in an outpatient setting. In order cause the intragastric balloon 109 to deflate, the physician activates the valve opening mechanism remotely and from outside the body, using a remote control 100 (FIG. 9). The physician holds remote control 100 near the stomach of the patient, and upon depression of a button, remote control 100 sends an activation signal to the combined microelectronic control and power source 115.

Combined microelectronic control and power supply 115 has an antenna (not shown) for receiving the activation signal from remote control 100. Upon receiving the activation signal, combined microelectronic control and power source uses power to begin increasing the temperature of heating element(s) (not shown) that are connected to the torsional spring 113. Similar to the embodiments discussed above that incorporate heating elements, metal film heating elements utilizing materials such as nichrome, stainless steel, copper, gold, or other such materials, can be used for the heating element(s). As the temperature of the heating element(s) begin to increase, the temperature of shape memory torsional spring 113 also begins to increase, thereby causing the spring to deform and reduce in diameter. As the diameter decreases, the seal between valve capsule 111 and balloon collar 114 is broken.

Once the seal between the balloon collar 114 and valve capsule 111 is broken and the valve capsule is separated from the shell, fluid contained inside the balloon freely flows through the opening 116 (FIG. 10*b*) that is created by the separation of the two portions. Through the normal movements and contraction of the stomach walls, the balloon will drain of the fluid contained inside and shrink down to a size that is passable through the human body. The combined microelectronic control and power supply and heating element(s) are safely contained within the valve capsule such that they do not present any danger to the patient. Because the entire intragastric balloon may now be in two separate pieces—an empty shell and a self-contained valve capsule—the passing of the balloon and valve is facilitated.

As with the previous embodiments described, in addition to performing the function of controlling the heating elements, the combined microelectronic control and power supply 115 may communicate with the remote control 100 to confirm that the deflation mechanism has been activated. Following receipt of a confirmation signal, the physician and patient may then track the progress of the passing of the device.

Figure 11:
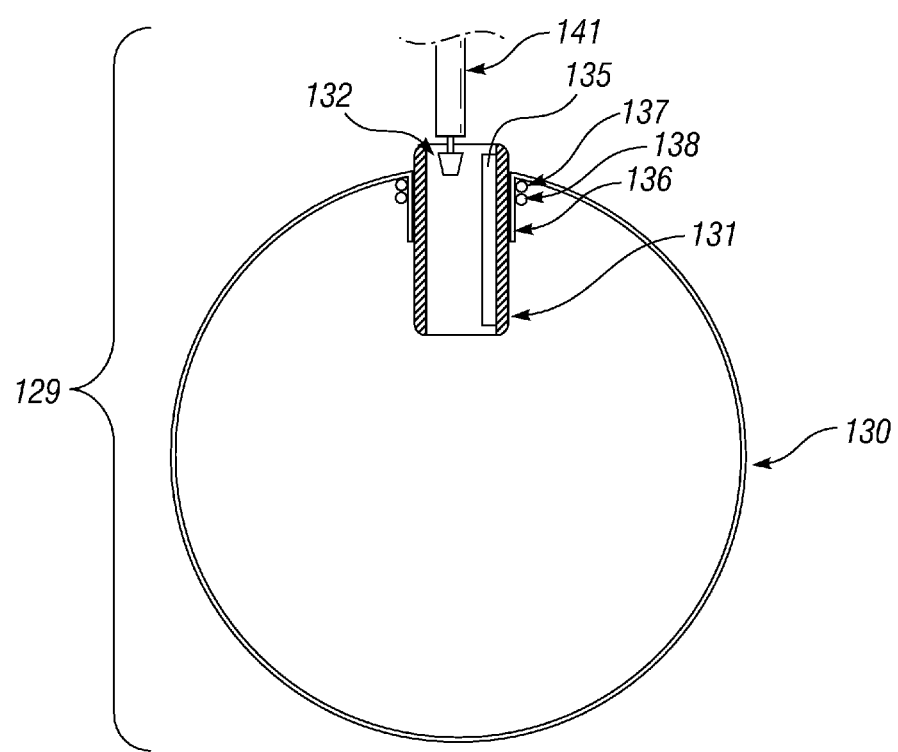
FIG. 11 is a side cut-away view of a remote-deflating intragastric balloon according to still a further embodiment of the present invention, which shows the balloon in the "closed" position.

Referring to FIG. 11, another embodiment of an intragastric balloon of the present invention incorporating a remote deflation mechanism is shown. Intragastric balloon 129 is comprised of shell 130 and valve capsule 131. Valve capsule 131 is comprised of valve 132, and combined microelectronic control and power source 135. Shell 130 is comprised of a collar 136, heating element 137, and shape memory cutting element 138. FIG. 11 also shows adjustment tool 141 for adjusting the volume of the intragastric balloon 129.

As with several of the other embodiments previously discussed, rather than using a remote deflation mechanism to open the valve of the intragastric balloon, the embodiment of the present invention shown in FIG. 11 utilizes a deflation mechanism for separating the entire valve capsule from the remaining portion of the balloon. When inflated, the valve capsule 131 is held tightly in the balloon collar 114 by pressure exerted by shape memory element 138, creating a seal between the valve capsule and the balloon collar.

Similar to the various procedures described above, at the time the physician desires to deflate the balloon, the patient may be brought into the physician's office in an outpatient setting. In order cause the intragastric balloon 129 to deflate, the physician activates the valve opening mechanism remotely and from outside the body, using a remote control 100 (FIG. 9). The physician holds remote control 100 near the stomach of the patient, and upon depression of a button, remote control 100 sends an activation signal to the combined microelectronic control and power source 135.

Combined microelectronic control and power supply 135 has an antenna (not shown) for receiving the activation signal from remote control 100. Upon receiving the activation signal, combined microelectronic control and power source uses power to begin increasing the temperature of heating element(s) 137 that are connected to the shape memory cutting element 138. Similar to the embodiments discussed above that incorporate heating elements, metal film heating elements utilizing materials such as nichrome, stainless steel, copper, gold, or other such materials, can be used for the heating element(s). As the temperature of the heating element(s) begin to increase, the temperature of shape memory cutting element 138 also begins to increase, thereby causing the cutting element to cut through the balloon collar 136. With the balloon collar 136 completely cut, the seal between valve capsule 131 and balloon collar 136 is broken.

Once the seal between the balloon collar 136 and valve capsule 131 is broken and the valve capsule is separated from the shell, fluid contained inside the balloon freely flows through the opening that is created by the separation of the two portions. Through the normal movements and contraction of the stomach walls, the balloon will drain of the fluid contained inside and shrink down to a size that is passable through the human body. The combined microelectronic control and power supply and heating element(s) are safely contained within the valve capsule such that they do not present any danger to the patient. Because the entire intragastric balloon may now be in two separate pieces—an empty shell and a self-contained valve capsule—the passing of the balloon and valve is facilitated. As an alternative to the cutting mechanism described herein, the remote deflation mechanism may be comprised of a mechanical system (such as a torsional spring) contained within the collar which holds the valve capsule in place until the balloon deflation mechanism is initiated.

As with the previous embodiments described, in addition to performing the function of controlling the heating elements, the combined microelectronic control and power supply 135 may communicate with the remote control 100 to confirm that the deflation mechanism has been activated. Following receipt of a confirmation signal, the physician and patient may then track the progress of the passing of the device.

To ensure the device of the present invention will pass easily, the intragastric balloon of the present invention may be constructed of a very thin, highly acid-resistant shell material. In addition, the intragastric balloon may be shaped to encourage collapse into a bullet shape for smooth passage through the intestines. This shape may be created by pre-formed convolutions in the shell that would expand into a substantially spherical or ellipsoidal shape when inflated, but would retract into its small collapsed shape when the remote deflation mechanism was triggered.

The remote control will take the form of a handheld control unit that may feature an LCD display and/or similar type of display and a control panel, such as a keyboard or touchscreen, to operate the device. The remote control may feature a series of menus that allow an operator to program (or read/determine) the microelectronics to contain in memory important information such as the intragastric balloon's size, patient's name, implanting physician, and the date it was implanted. The remote control may communicate with the sensor via telemetry through radiowaves. The FDA and globally recognized communications band (WMTS 402-405 Mhz) may be used in some embodiments, and an authentication process (e.g., digital handshake signal, PIN verification, or other similar verification process) can be used to ensure that the device cannot be accidentally accessed or controlled by another control mechanism other than the remote control. The telemetry control signal can be sent from approximately a foot or possibly a greater distance from the patient and will typically not require the patient to disrobe to query the sensor or to change its parameters. The remote control may be able to read and write information to the microelectronics contained in the intragastric balloon. The remote control may also be password controlled to prevent unauthorized personnel from querying the device. The display of the remote control, which may include visual and audio outputs, typically will display or output the sensed parameter of the remote deflation valve's condition or physical parameter whether this parameter is "open," "closed," or any other physical parameter that the remote control is adjusted to monitor.

EXAMPLES

The following examples describe various procedures using the method and device of the present invention.

Example 1

Remote Deflation of an Intragastric Balloon Containing a Sealing Plug

In this example, the patient is an overweight male who has previously had an intragastric balloon inserted into his stomach. The intragastric balloon has been implanted for a full course of treatment for six months, and the surgeon is prepared to remove the balloon.

The removal of the balloon is performed in an outpatient setting at the doctor's office. Reference is made to FIGS. 2a and 2b for the remote deflation valve utilized in this example.

In order to open deflation valve 16, the physician activates the remote deflation mechanism from outside the body using a remote control 100, such as that depicted in FIG. 9. The physician holds remote control 100 near the stomach of the patient, and upon depression of a button, remote control 100 sends an activation signal through the patient's tissue to the microelectronic control 32.

Upon receiving the activation signal, microelectronic control 32 uses power from a battery 33 to begin increasing the temperature of heating element(s) 31. As the temperature of heating element(s) 31 begins to increase, the wax plug 30 begins to melt.

As the wax begins to melt, it collects on wicking surfaces 34. The collection of the wax on wicking surfaces 34 prevents the wax from clogging capillaries 35 and allows the fluid contained within intragastric balloon 10 to flow out of the balloon. Once the wax is melted and collected on wicking surfaces 34, capillaries 35 allow the free flow of the fluid contained inside the balloon through valve opening 36. In addition, once the wax is melted, the microelectronic control 32 sends a confirmation signal to the remote control 100, informing the doctor and patient that the deflation device has been activated.

Through the normal movements and contraction of the stomach walls, the balloon drains of the saline contained inside and shrinks down to a size that is passable through the human body. The microelectronics, heating elements, and battery are safely contained within the valve structure such that they do not present any danger to the patient.

Having received the confirmation signal, the patient may now leave the doctor's office and return home. The patient tracks the passage of the intragastric balloon and informs the doctor when it has passed.

Example 2

Remote Deflation of an Intragastric Balloon Containing a Separable Valve

In this example, the patient is an overweight female who has previously had an intragastric balloon implanted. After implantation the patient has experienced significant undesired side effects resulting from the implantation, including nausea, vomiting, and general abdominal discomfort. Therefore, the patient desires to have the remote deflation mechanism activated, thus allowing the balloon to be passed.

As with the first example, the balloon removal is performed in an outpatient setting at the doctor's office. Reference is made to FIGS. 8*a* and 8*b* for the remote deflation mechanism utilized in this example.

In order to cause the intragastric balloon 90 to deflate, the physician activates the remote deflation mechanism using a remote control 100, such as that depicted in FIG. 9. The physician positions remote control 100 near the stomach of the patient, and upon depression of a button, remote control 100 sends an activation signal through the tissue of the abdominal cavity to the microelectronic control 95.

Microelectronic control 95 has an antenna for receiving the activation signal from remote control 100. Upon receiving the activation signal, microelectronic control uses power from battery 96 to begin increasing the temperature of heating element(s) 93. As the temperature of heating element(s) 93 begins to increase, the temperature of cutting wire 94 also begins to increase. The increased temperature of the cutting wire causes the valve/balloon bond 92 to deteriorate, resulting in separation of the valve 91 from shell 97.

As the valve/balloon bond 92 breaks and separates from the shell, the normal movements of the stomach cause the fluid contained inside the balloon to freely flow through the opening 98. The normal movements and contraction of the stomach walls cause the intragastric balloon to completely drain of the fluid contained inside and shrink down to a size that is passable through the human body. The microelectronics, heating elements and battery are safely contained within the valve structure such that they do not present any danger to the patient. Because the entire intragastric balloon may now comprise two separate pieces, the passing of the balloon and valve is facilitated.

Once the valve/balloon bond has been broken, the microelectronic control 95 sends a confirmation signal to remote control 100 to confirm that the deflation mechanism has been activated. Following receipt of a confirmation signal by the remote control, the procedure is complete and the patient can return home and wait until the shell and valve assembly pass through the system. The patient tracks the passage of the intragastric balloon and informs the doctor when it has passed.

Example 3

Remote Deflation of an Intragastric Balloon Containing a Valve Capsule

In this example, the patient is an overweight male who has previously had an intragastric balloon inserted into his stomach. The intragastric balloon has been implanted for a full course of treatment for six months, and the surgeon is prepared to remove the balloon.

The removal of the balloon is performed in an outpatient setting at the doctor's office. Reference is made to FIGS. 10*a* and 10*b* for the remote deflation valve utilized in this example.

In order to deflate balloon 109, the physician activates the remote deflation mechanism from outside the body using a remote control 100, such as that depicted in FIG. 9. The physician holds remote control 100 near the stomach of the patient, and upon depression of a button, remote control 100 sends an activation signal through the patient's tissue to the combined microelectronic control and power source 115.

Upon receiving the activation signal, the combined microelectronic control and power source 115 uses power to begin increasing the temperature of heating element(s) (not shown) that are connected to the torsional spring 113. As the temperature of the heating element(s) begin to increase, the temperature of shape memory torsional spring 113 also begins to increase, thereby causing the spring to deform and reduce in diameter. As the diameter decreases, the seal between valve capsule 111 and balloon collar 114 is broken. The valve capsule is separated from the shell, and fluid contained inside the balloon freely flows through the opening 116 (FIG. 10*b*) that is created by the separation of the two portions.

Through the normal movements and contraction of the stomach walls, the balloon drains of the saline contained inside and shrinks down to a size that is passable through the human body. The combined microelectronics control and power supply and heating element(s) are safely contained within the valve capsule such that they do not present any danger to the patient.

Having received the confirmation signal, the patient may now leave the doctor's office and return home. The patient tracks the passage of the intragastric balloon and informs the doctor when it has passed.

To more effectively manage use of intragastric balloons, the present invention also utilizes sensors on the balloon to monitor conditions within or external to the balloon. Sensors that can be used include pressure, temperature, pH, glucose, position, and other sensors for monitoring physical conditions. For example, by monitoring the internal balloon pressure, the physician can verify that the balloon remains intact and that there is not a leak in the system. The sensors may be provided on the above-described balloons that are remotely deflated, but also may be useful on intragastric balloons that are conventionally deflated using an esophageal catheter. That is, the aforementioned internal balloon pressure sensor is useful for detecting pressure losses within any intragastric balloon. Likewise, although the sensors illustrated herein are described as being incorporated in a deflation valve, they could alternatively be incorporated into the shell wall of the balloon, inside the shell, or into a fill valve. The location of the sensor depends on the area from which measurements will be taken, so for instance to monitor internal balloon conditions a sensor may be mounted inside the shell or just inside the deflation valve. Various arrangements including multiple sensors are contemplated and within the skill of those in the art.

The particular sensors used, as mentioned, may take numerous forms. For example, suitable sensors are described in U.S. Pat. Nos. 7,141,016 and 7,160,258, whose disclosures are hereby expressly incorporated by reference. Any of the sensors that may be used may transmit signals from inside the body to an external monitor. As such, an exemplary sensor incorporates a transmitter that actively transmits a wireless radio frequency (RF) signal that may be detected by an external receiver coupled to a monitor (not shown). Details of such RF communication systems are well-known in the art, and will not be described further herein.

To gather data from the various sensors, a system of the present invention would include an external handheld device that could remotely query the sensors. For example, the physician may utilize the remote control 100 shown in FIG. 9 to stimulate one or more sensors to provide a pressure reading. Such real-time information is useful during routine checkups, and also during the deflation sequence. The sensors coupled to microchips may be capable of reading and writing data so that the physician can query the sensor for historical pressure information and add adjustment data to a system that self-adjusts the balloon. The sensors may also be coupled to an internal power source so as to enable self queries and routine recordation of pressure data. The sensor and accompanying microchip may be provided with the ability to self-diagnose and periodically self-adjust based on the self-queries and subsequent data analysis. This mode of operation of the system may be used in conjunction with periodic remote control by a physician to ensue the system is functioning autonomously. Alternatively, pressure data can be downloaded after the device has successfully been removed or passed through the patient for diagnosis and analysis purposes.

Figure 12:
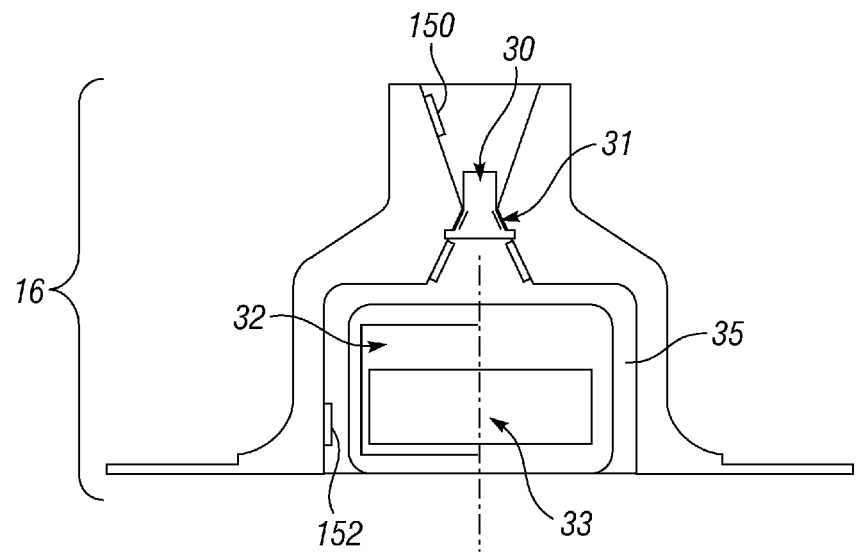
FIG. 12 is a side cut-away view of a remote deflation valve according to one embodiment of the present invention, which shows the valve in the "closed" position and one or more sensors in the deflation valve to monitor conditions within and/or external to the balloon.

FIG. 12 is a side cut-away view of the remote deflation valve 16 seen in FIG. 2a that can be used with the intragastric balloons of the present invention. To reiterate, the valve 16 comprises a sealing plug 30, heating element(s) 31, microelectronic control 32 and power source 33. In addition, a sensor 150 positioned at the external mouth of the valve 16, outside the sealing plug 30, monitors conditions outside of the valve 16, for example in the patient's stomach. By monitoring the pressure inside the stomach, the physician can determine whether there are changes in peristalsis and therefore determine whether the balloon volume should be increased or decreased to induce further satiety.

Additionally, FIG. 12 illustrates a sensor 152 positioned internal to the sealing plug 30, such as in one of the capillaries 35. The internal sensor 152 can monitor conditions inside the balloon. For instance, by monitoring balloon pressure, the physician can verify that the balloon is still intact and that there is no leak in the system. Furthermore, the internal sensor 152 can be used to verify that the remote deflation operation is successful. Moreover, the sensor 152 can monitor internal balloon pressure to determine whether the balloon volume should be increased or decreased.

The balloon volume can be adjusted by their manual means, such as by using an esophageal catheter, remotely by a pump (not shown), or by tonicity. To increase the volume by tonicity, salt may be added to the balloon which has a semipermeable shell. Tonicity is the osmotic pressure or tension of a solution, usually relative to that of blood. In the present invention, the osmotic pressure of the fluid within the balloon may be adjusted relative to the fluid within the stomach, outside of the balloon. The addition of salt would therefore cause fluid to be slowly drawn inside the balloon through the shell wall as the system tries to reach equilibrium inside and outside the shell. Additionally, where the sensor 150 monitors pressure, a microchip could also be used to self-adjust the balloon volume and pressure relative to pressure data that is collected inside or outside of the balloon based on an algorithm that meets the requirements for satiety.

Figure 13:
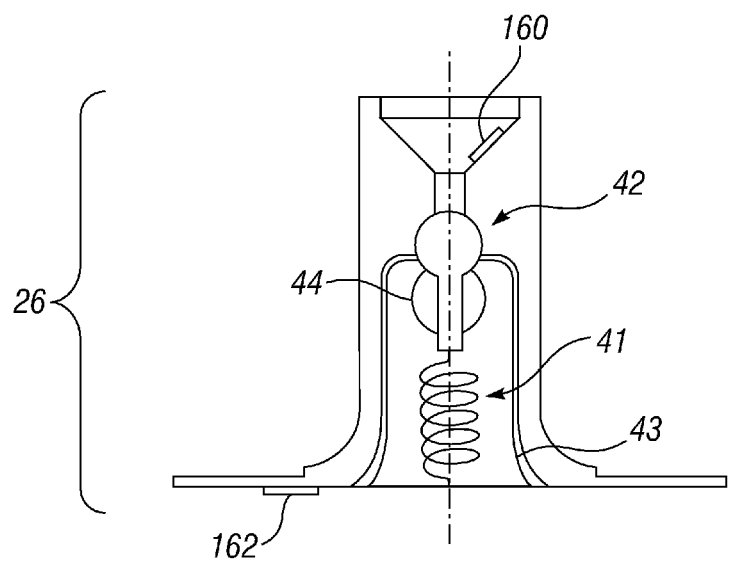
FIG. 13 is a side cut-away view of a remote deflation valve according to a further embodiment of the present invention, which shows the valve in the "closed" position and one or more sensors in the deflation valve to monitor conditions within and/or external to the balloon.

FIG. 13 is a side cut-away view of the remote deflation valve 26 seen in FIG. 3a that can be used with the intragastric balloons of the present invention. To reiterate, the valve 26 includes a shape memory spring 41, plug 42, and capillaries 43. In addition, a sensor 160 positioned at the external mouth of the valve 26, outside the plug 42, monitors conditions outside of the valve 26, for example in the patient's stomach. A second sensor 162 is located on the inner surface of the valve 26, internal to the balloon shell to which the valve attaches (not shown). The sensors 160, 162 provide the same functionality as the sensors 150, 152 of FIG. 12.

Figure 14:
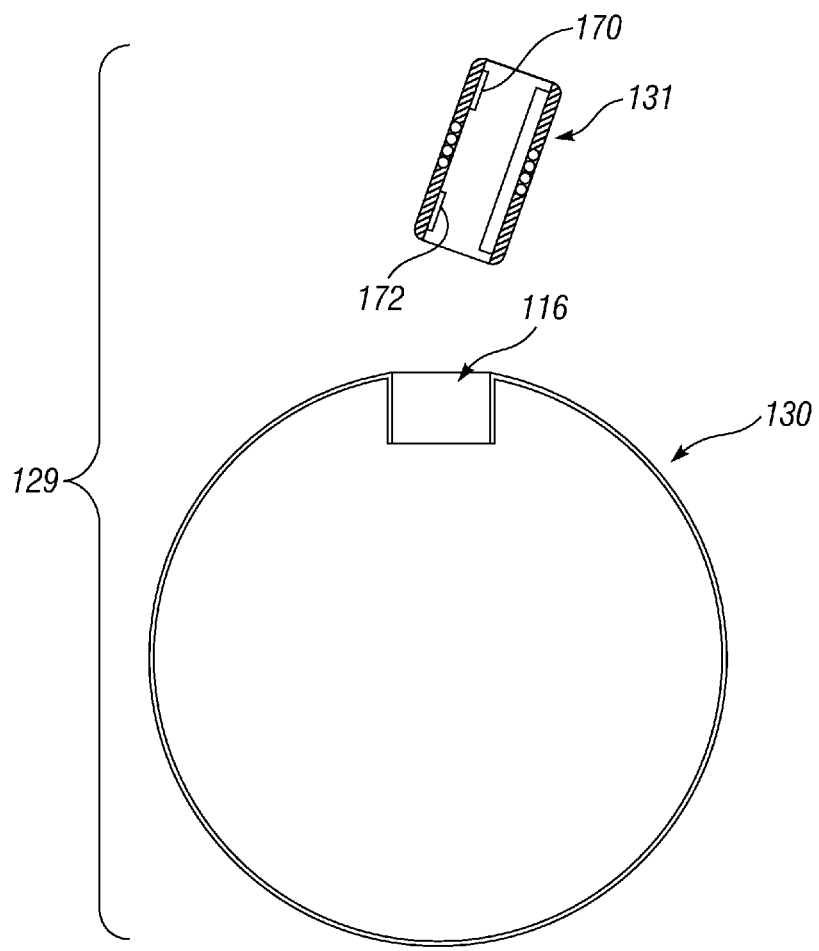
FIG. 14 is a side cut-away view of the remote-deflating intragastric balloon of FIG. 10a shown in the "open" position, in which one or more sensors in a deflation valve monitor conditions within and/or external to the balloon, and during passage through the intestinal tract.

FIG. 14 is a side cut-away view of the remote-deflating intragastric balloon 129 of FIG. 10a shown in the "open" position, in which two sensors 170, 172 in a deflation valve 131 may monitor conditions within and/or external to the balloon shell 130, and during passage through the intestinal tract. The two sensors 170, 172 are positioned within the valve 131 to measure, respectively, conditions external and internal to the valve/shell combination. That is, as described above, the sensors 170, 172 may each be used to monitor a condition, e.g., pressure, within the shell 130 or within the patient's stomach.

Furthermore, after the deflation valve 131 separates from the shell 130, the sensors 170, 172 therein may monitor conditions as the valve passes through the gastrointestinal tract. For example, the sensors 170, 172 could record pressure measurements along the gastrointestinal tract to detect any anomalies such as strictures, growths, or obstructions.

Figure 15:
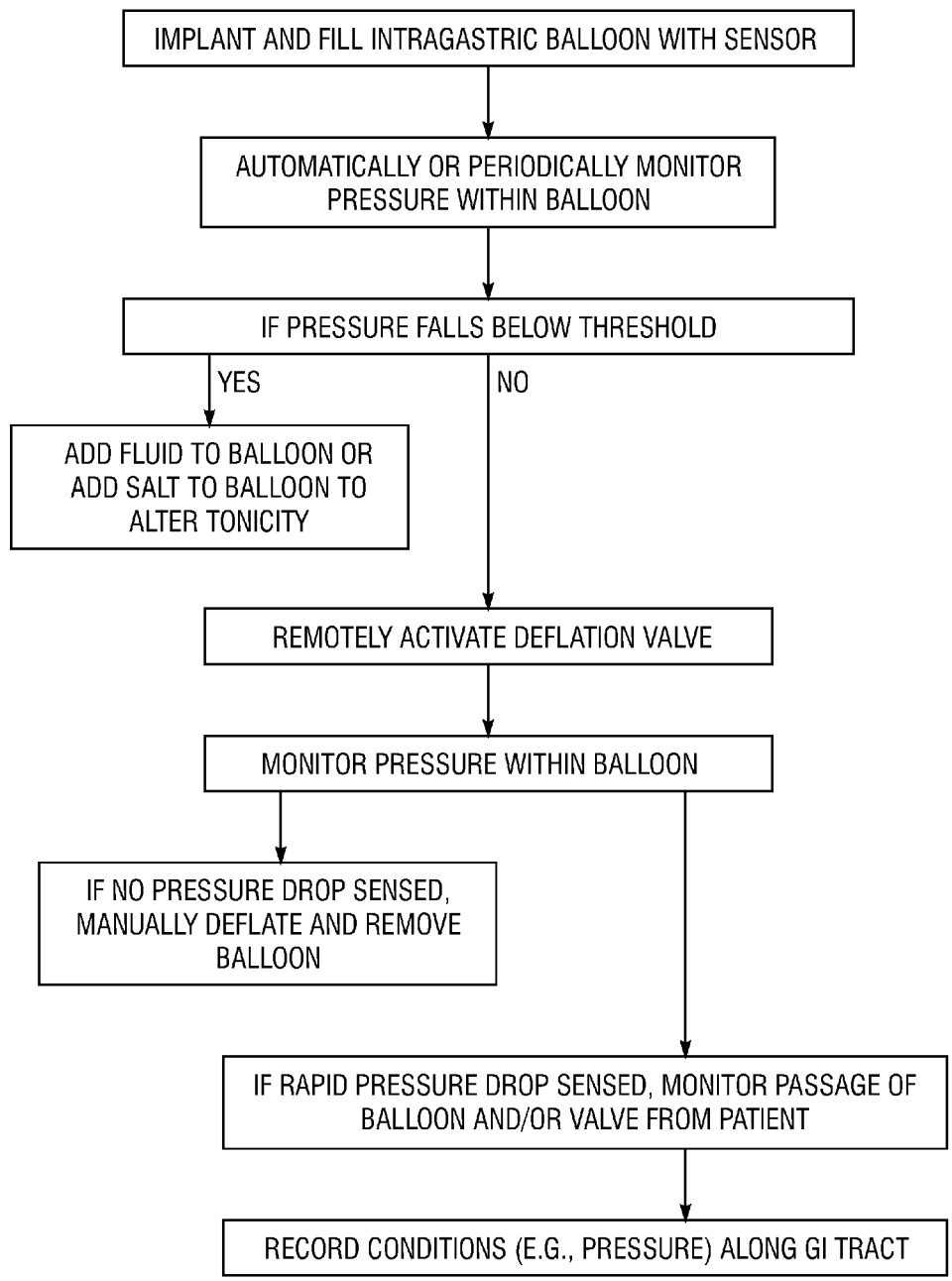
FIG. 15 is a flow chart illustrating several techniques for monitoring conditions, including pressure, in and around an intragastric balloon of the present invention.

FIG. 15 is a flow chart illustrating several techniques for monitoring conditions, including pressure, in and around an intragastric balloon of the present invention. Note the capacity to monitor pressure as the sensor passes through the GI tract.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. A method for facilitating weight loss in a patient comprising the steps of:
    inserting an intragastric balloon into a patient's stomach, the intragastric balloon comprising
        a shell defining an adjustable volume for containing a fluid, and
        a valve capsule, sealed to the shell, for enabling adjustment of the shell volume and including a sensor arrangement,
        the valve capsule being entirely separable from the shell by remote activation; and
    sensing pressure within the shell volume while the valve capsule is sealed to the shell, and
    sensing pressure in a digestive track of the patient after separation of the valve capsule from the shell.

2. The method of claim 1, further comprising remotely adjusting the volume of fluid in the shell in response to the sensed pressure within the shell volume, and external to the shell volume.

3. The method of claim 1, further comprising:
sensing a pressure external to the shell volume when the valve capsule is sealed to the shell.

4. A method for facilitating weight loss in a patient comprising the steps of:
inserting an intragastric balloon into a patient, the balloon comprising a shell for containing a fluid, and a valve capsule sealed to the shell and containing a sensor arrangement;
introducing a fluid into the shell;
monitoring pressure within the shell while the valve capsule is sealed to the shell;
based on pressure readings, adding or removing fluid from the shell;
deflating the shell by entirely separating the valve capsule from the shell by remote activation; and
during the deflating step, monitoring pressure within the shell volume by means of the sensor arrangement.

5. The method of claim 4 further comprising the step of sensing pressure in a digestive track of the patient after separation of the valve capsule from the shell, by means of the sensor arrangement.

\* \* \* \* \*